(12) United States Patent
McLean et al.

(10) Patent No.: US 6,375,463 B1
(45) Date of Patent: *Apr. 23, 2002

(54) DENTAL WEDGES HAVING PROXIMAL ENDS WITH GRITTY TOP LAYERS

(75) Inventors: Bruce McLean; Dan E. Fischer, both of Sandy, UT (US)

(73) Assignee: Ultradent Products, Inc., South Jordan, UT (US)

(*) Notice: Subject to any disclaimer, the term of this patent is extended or adjusted under 35 U.S.C. 154(b) by 0 days.

This patent is subject to a terminal disclaimer.

(21) Appl. No.: 09/707,183

(22) Filed: Nov. 6, 2000

Related U.S. Application Data

(63) Continuation-in-part of application No. 09/064,457, filed on Apr. 22, 1998, now Pat. No. 6,142,781, which is a continuation-in-part of application No. 09/505,930, filed on Feb. 14, 2000, now abandoned, which is a continuation-in-part of application No. 09/356,629, filed on Jul. 19, 1999, now abandoned.

(51) Int. Cl.[7] ............................................. A61C 7/00
(52) U.S. Cl. ..................................................... 433/149
(58) Field of Search ........................... 433/39, 40, 149, 433/155

(56) References Cited

U.S. PATENT DOCUMENTS

| 109,665 A | 11/1870 | Richards |
| 350,150 A | 10/1886 | Parr ........................... 433/149 |
| 421,925 A | 2/1890 | Graves |
| 523,136 A | 7/1894 | Trakofler |
| 1,529,075 A | 3/1925 | McIntrye |
| 1,657,497 A | 1/1928 | Cichon |
| 2,083,131 A | 6/1937 | Tornebohm |
| 2,150,005 A | 3/1939 | McNinch ..................... 433/149 |
| 3,193,094 A | 7/1965 | Schulstad ................... 433/149 |
| 3,473,226 A | 10/1969 | Arlers ......................... 433/149 |
| 3,510,948 A | 5/1970 | Walthall ...................... 433/149 |
| 3,636,631 A * | 1/1972 | Tofflemire |
| 3,815,243 A | 6/1974 | Eames ............................ 32/63 |
| 4,337,041 A | 6/1982 | Harsany ...................... 433/149 |
| 4,696,646 A | 9/1987 | Maitland ..................... 433/149 |
| 4,878,508 A * | 11/1989 | Durbin ........................ 433/149 |
| 5,230,263 A | 7/1993 | Kwaka ........................ 81/125.1 |
| 5,448,932 A | 9/1995 | Zurbuchen et al. ........ 81/124.4 |
| 5,836,767 A | 11/1998 | Aspel .......................... 433/141 |
| 5,890,900 A | 4/1999 | Fischer et al. .............. 433/149 |
| 5,890,901 A | 4/1999 | Fischer et al. .............. 433/149 |
| 6,142,781 A * | 11/2000 | Fischer ........................ 433/149 |
| 6,234,793 B1 * | 5/2001 | Brattesani et al. ............ 433/39 |

* cited by examiner

*Primary Examiner*—Ralph A. Lewis
(74) *Attorney, Agent, or Firm*—Workman, Nydegger & Seeley

(57) ABSTRACT

Improved dental wedges having gritty top layers are disclosed that enable instruments to easily engage the dental wedges and position them between the two teeth. The wedges may have gritty layers that are positioned on their proximal ends through use of an adhesive or by molding techniques. Each gritty top layer includes a grit material such as aluminum dioxide and an attachment material such as acrylics.

20 Claims, 7 Drawing Sheets

DENTAL WEDGES HAVING PROXIMAL ENDS WITH GRITTY TOP LAYERS

RELATED APPLICATIONS

This application is a continuation-in-part patent application of U.S. Pat. application Ser. No. 09/064,457 now U.S. Pat. No. 6,142,781 entitled Dental Instruments for Use with Dental Wedges which was filed on Apr. 22, 1998 on behalf of Dan E. Fischer. Ser. No. 09/064,457 is incorporated herein by specific reference.

This application is also a continuation-in-part patent application of U.S. patent application Ser. No. 09/505,930 entitled Systems for Holding Textured Dental Matrix Bands and Related Methods which was filed on Feb. 14, 2000 on behalf of Steven J. Brattesani and Dan E. Fischer and now abandoned. Ser. No. 09/505,930 is incorporated herein by specific reference. Ser. No. 09/505,930 is a continuation-in-part patent application of U.S. patent application Ser. No. 09/356,629 entitled Dental Matrix Retainer Clamps with Improved Visibility which was filed on Jul. 19, 1999 on behalf of Dan E. Fischer and is now abandoned. Ser. No. 09/356,629 is incorporated herein by specific reference.

BACKGROUND

1. Field of the Invention

The invention disclosed herein are in the field of dental instruments. More particularly, the inventions relates to dental wedges which are utilized to separate teeth in preparation for a dental procedure involving the use of dental matrix bands that are positioned around a dental preparation to act as a form for the material used to fill the preparation.

2. Background Art

In the field of dentistry, dental practitioners often treat patients who have developed cavities on the side of a tooth. When these cavities are located adjacent to neighboring teeth they are known as interproximal cavities. In order to treat cavities on the sides of teeth such as interproximal cavities, the dental practitioner removes the infected portion of the tooth, then deposits a filling such as a resinous material or an amalgam into the tooth preparation.

In order to properly deposit the filling without undesired seepage of the filling material beyond the side of the tooth, typically a matrix band is disposed about the tooth, after which the filling material is deposited. A matrix band is typically a metallic or plastic strip having first and second ends which are joined, thereby forming a mold which is disposed about the tooth. When encircled about the tooth, the matrix band acts as a form, similar in function to a concrete form, providing a mold for the desired shape of the repaired tooth.

In order to maintain the matrix band in a desired position with respect to the tooth to be repaired, small dental wedges are often placed in the interproximal spaces between the matrix band and the teeth adjacent the tooth to be repaired. The wedges also space the teeth adjacent to the tooth to be repaired during the filling procedure. Dental wedges may be used to spread adjacent teeth for a variety of other purposes such as enabling a dental matrix band to be initially positioned around a tooth. Due to the elasticity of the periodontal fibers the teeth will resume their original position after the wedges and matrix bands are removed.

FIG. 1 depicts a tooth 10 encircled by a dental matrix band 20. A dental wedge 30 is shown being positioned between tooth 10 and adjacent tooth 12. Pliers 18 are used to hold wedge 30. FIG. 2 shows a typical matrix band at 20 before being placed around a tooth. FIG. 3 shows dental wedge 30 in more detail.

The matrix bands can also be formed from different materials to yield different properties. Traditionally, matrix bands have been prepared from stainless steel. Increasing amounts of matrix bands are being sold which are transparent or translucent to enable radiant energy to pass through the band toward composite material in a preparation to polymerize the composite material.

A significant problem with the use of conventional matrix bands and dental wedges is the tendency of the dental wedges to slip out of their positions in the interproximal spaces. When the wedges slip out from between the teeth, the desired configuration of the restored tooth may be distorted Another problem related to the interface between wedges and dental matrix bands is the potential for injurious slippage during insertion of a wedge. These problems are not solved by the prior art.

In addition to the prior art wedge shown in FIG. 3, FIGS. 4–5 depict other examples of prior art wedges respectively at 40 and 50 and are discussed hereinbelow. Typical wedges have a triangular cross section as shown. This triangular cross section includes a thin apex at the distal insertion end which widens into a flat base at the other end, the proximal gripping end. Each wedge in FIGS. 3–5 is depicted as having a distal insertion end, respectively shown at 32, 42 and 52 and a proximal gripping end, shown respectively at 34, 44 and 54.

As shown in FIG. 1, a wedge is typically placed with the widened end located toward the gum line and with the thin apex extending between the teeth and away from the gums in order to fit properly in an interproximal space. When using such dental wedges, the practitioner is careful to orient the wider end toward the gumline while the more thinner, pointed apex is directed upward between the teeth.

In light of this triangular configuration of typical wedges, it is important to orient the wedge properly with respect to the interproximal space before pressing the body of the wedge, shown respectively in FIGS. 3–5 at 36, 46 and 56, into the interproximal space. In addition, the properly oriented wedge must be precisely guided into the space. However, it is often difficult to orient the wedges correctly within the desired interproximal space in the mouth due to their small size and the difficulty involved in controlling the insertion of the wedge without making the patient uncomfortable or possibly damaging the gums and/or teeth of the patient. Accordingly, a practitioner maintains a solid grip on the wedge in order to strategically align and properly guide the wedge. Of course, it is also necessary for the practitioner to maintain a solid grip on the wedge to avoid dropping the wedge.

The tendency of these wedges to slip due to their shape is further increased due to their smoothness and relative rigidity when tightly gripped, particularly when covered with fluids, such as saliva or blood. Such smoothness and rigidity inherently result from the type of materials used to form conventional wedges. Typical dental wedges are comprised of a rigid plastic or wood, such as that from sycamore trees, having a smooth exterior surface which compounds the difficulties associated with firmly gripping the wedges due to their small size. Note that wedge 30 is formed from wood while wedge 40 is formed from a translucent plastic to enable light to pass through during light polymerization of a composite material Another example of a wedge that has translucent portions is disclosed in U.S. Pat. No. 5,743,738 issued to Baffelli et al., which is hereby incorporated by reference.

A practitioner typically uses small-nosed pliers, known as cotton pliers, to grip a particular wedge and to position the wedge within the mouth. To enhance an practitioner's ability to grasp a wedge, some wedges have a head disposed on the proximal end of the body of the wedge. For example, wedges 40 and 50, are shown respectively with heads 48 and 58 attached to bodies 46 and 56. Head 48 has four gripping surfaces, 49a–d, which makes it easier to grasp than head 58. However, since head 48 is typically comprised of a rigid material, such as plastic, pliers still readily slip when contacting such wedges.

After the wedge is initially positioned, the dentist forces the wedge into final position. During the forced insertion, the likelihood of injury is greatest as the pliers or tweezers may slip off the wedge into the soft tissues in a patient's mouth. Additionally, when the dentist attempts to regrasp the wedge with cotton pliers there is also risk of slipping off the wedge. The slippery nature of the wedge may cause the wedge to become dislodged within the patients' mouth or ejected from the pliers onto the floor such that is becomes contaminated.

As indicated above, the slippery nature of wedges combined with the conditions in the oral cavity sometimes enable the wedges to become dislodged after being positioned in an interproximal space. The tendency to be displaced after being positioned may also result from being used in very tight interproximal spaces which makes it difficult to insert a sufficiently significant portion of the body of the wedge into the space.

There is, therefore, a need in the art for a dental wedge which is easily positioned with minimal risk of the positioning instrument slipping off of the wedge.

BRIEF SUMMARY AND OBJECTS OF THE INVENTION

It is therefore an object of the invention to provide an improved dental wedge.

It is also an object of the invention to provide means for preventing slipping of a dental tool used to grip the wedge.

It is another object of the invention to provide a dental wedge which is easily grasped by a dental instrument, such as tweezers or cotton pliers.

One invention relates to a dental wedge, comprising: (i) a body having a distal insertion end; and (ii) a gritty top layer on the proximal end of the wedge. The dental wedge preferably has a head coupled to the body by a neck such that the gritty top layer is on the proximal end of the head. However, the gritty top layer may be on the proximal end of a wedge having any configuration.

The gritty top layer may be sufficiently compressible that it noticeably compress when an instrument is pushed against the gritty top layer as the tapered body is inserted within an interproximal space between two teeth. Additionally, the gritty top layer may be sufficiently hard that it does not noticeably compress when an instrument is pushed against the gritty top layer as the tapered body is inserted within an interproximal space between two teeth. In either embodiment, the gritty top layer essentially provides frictional resistance such that the dental instrument is prevented from slipping or sliding off of the gritty top layer.

The gritty top layer includes a grit material mixed in an attachment material. The attachment material may be an adhesive such that the gritty top layer is positioned on the proximal end of the wedge as a coating and then allowed to harden. The attachment material may also be a plastic such that the gritty top layer is positioned on the proximal end of the wedge by a molding process. Although, the gritty top layer may include any suitable grit material, the grit material preferably has an average particle size ranging from about 50 microns to about 80 mesh.

Additional objects and advantages of the invention will be set forth in the description which follows, and in part will be obvious from the description, or may be learned by the practice of the invention. The objects and advantages of the invention may be realized and obtained by means of the instruments and combinations particularly pointed out in the appended claims.

BRIEF DESCRIPTION OF TIE DRAWINGS

In order that the manner in which the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are therefore not to be considered limiting of its scope, the invention will be described with additional specificity and detail through the use of the accompanying drawings in which.

DETAILED DESCRIPTION OF THE PREFERRED EMBODIMENTS

Figure 1:
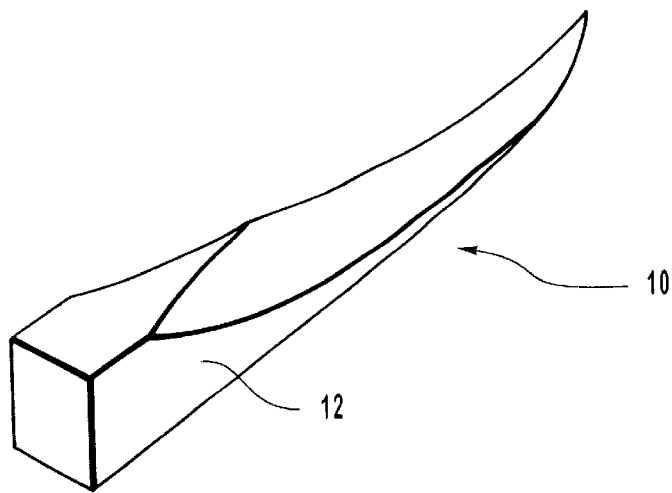
FIG. 1 is a view of a dental wedge of the prior art.

The wedge of the present invention is useful for maintaining a matrix band in a desired orientation, creating a space between teeth or providing other dental or non-dental functions. The wedges have a distal insertion end opposite from a proximal end. The wedges have a proximal end with a frictional resistance surface. The frictional resistance surface is preferably a gritty or grainy top layer on the proximal end that enables a practitioner to safely position the dental wedge between teeth.

The gritty top layer is identified in the accompanying drawings at 70. Gritty top layer 70 includes a grit material such as grains or particulates. The top layer is formed by mixing the grit material with an attachment material to form a mixture and then applying the mixture onto the proximal end of the wedge. The top layer is preferably applied as a coating that hardens after being applied onto the proximal end of the wedge. The top layer may also be molded onto the dental wedge.

The grains or particulates in gritty top layer 70 may be any suitable grit material capable of providing increased friction. Examples of preferred grit materials include aluminum oxide, pumice, silica, titanium dioxide, etc. While the grit materials may have any suitable color, for example, the aluminum oxide may be black or reddish brown, however, aluminum oxide is preferably used that is white. The grains may have any suitable size. The preferred average particle size ranges from about 50 microns to about 80 mesh.

When gritty top layer 70 is formed from a coating that is applied on the wedge as a mixture of a grit material and an attachment material, the attachment material may be any suitable adhesive. The adhesive is preferably a light activated adhesive so that the mixture may be applied onto the wedge and then activated. The adhesive is also preferably flexible. The adhesive is preferably a flexible light cured acrylic. Other adhesives that may also be used include epoxies and in some instances silicones may be used. When gritty top layer 70 is formed by molding, the attachment material may be any suitable moldable material. The preferred moldable material is urethane. Thermoplastic elastomers are generally useful as moldable materials. Additional examples include elastomers such as neoprene, silicone, polypropylene, latex, rubber, etc.

Gritty top layer 70 may be relatively hard or compressible. An advantage of a compressible gritty top layer is that the instrument used to engage gritty top layer 70 can push into it. FIG. 5C depicts blunt end 84 of tweezers 80 being used to push against gritty top layer 70. If gritty top layer 70 is compressible as discussed above, then blunt end 84 of tweezers 80 indents into gritty top layer 70 which increases the surface area contacted by the instrument so that there is even less likelihood of the instrument sliding off gritty top layer. While a compressible gritty top layer further decreases the potential for slipping, it is not necessary for gritty top layer 70 to be compressible since the grit material in gritty top layer 70 provide significant frictional engagement. Accordingly, gritty top layer 70 may sufficiently hard or compressible that it either does not or does noticeably compress when an instrument is pushed against the gritty top layer as the tapered body means is inserted within an interproximal space between two teeth.

The gritty top layer may have any suitable shape. For example, the gritty top layer may be primarily flat or have a curved configuration. Examples of curved configurations include gritty top layers that are essentially convex or domed, and gritty top layers that are essentially concave or dimpled. A dome-shaped gritty top layer may be useful when formed to be compressible while a dimpled gritty top layer may be useful when formed to be relatively hard as a dental instrument may easily be positioned at or near the low point in dimpled gritty top layer in a manner such that the concavity assists in preventing a dental instrument from slipping off of gritty top layer 70. The degree of convexity or concavity can be relatively shallow or relatively deep.

Figure 2:
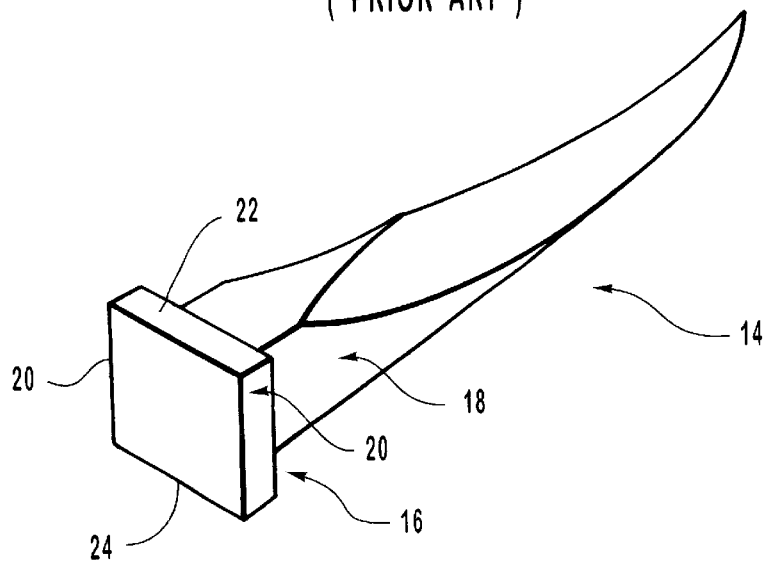
FIG. 2 is a view of another dental wedge of the prior art.
Figure 3:
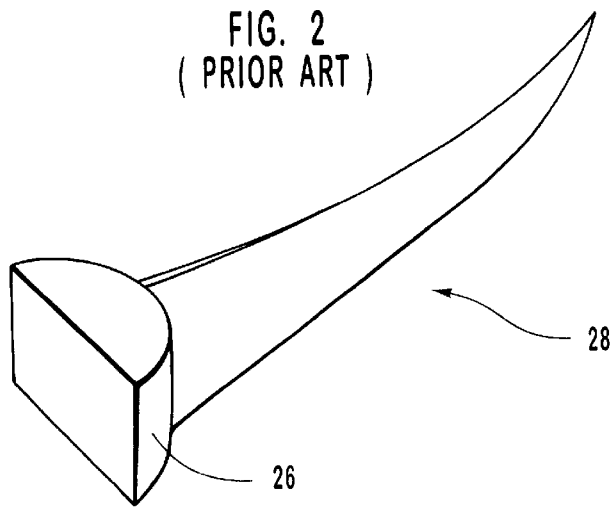
FIG. 3 is a view of yet another dental wedge of the prior art.

A gritty top layer such as gritty top layer 70 may be used in association with any dental wedge. For example, the gritty top layer may be applied to the proximal end of any prior art dental wedge such as those shown in FIGS. 1–3. Similarly, the gritty top layers disclosed herein may also be applied to the proximal ends of other conventional dental wedges such as those disclosed in U.S. Pat. No. 5,743,738 issued to Baffelli et al. and U.S. Pat. No. 5,421,725 issued to von Weissenfluh. However, the dental wedge is preferably configured in a similar fashion to those disclosed in U.S. Pat. Nos. 5,890,900 and 5,890,901 both of which are assigned to Ultradent Products, Inc. Examples of such wedges, as disclosed in these patents owned by Ultradent Products, Inc., are discussed in detail below with reference to the drawings.

Since the gritty top layer is positioned on the proximal end of the wedge, the wedge may be formed from any suitable material such as wood. For example, the gritty top layer may be adhered to the proximal end of wedge 10. However, the wedge is preferably formed integrally from plastic. More particularly, since the body of the wedge is configured to be disposed within an interproximal space and to maintain a matrix band in a desired orientation between adjacent teeth or otherwise maintain a space between teeth, the body is preferably comprised of a rigid material, such as a relatively rigid plastic. An example of a suitable plastic is nylon. In addition to ease of manufacturing, an advantage of using plastics to form the wedge is that plastics may be selected such that the wedge is entirely translucent or only a portion thereof may be translucent such as the body to enable light to be directed through the wedge.

A wedge formed from plastic may be formed by any means, such as thermoplastics or cast plastics formation techniques. One skilled in the art will appreciate that a variety of different methods are available for manufacturing the dental wedges. When top layer 70 is molded, the two components used to form top layer 70 and the remainder of the wedge are molded to each other, such as by using a two-color mold to cause the components to chemically adhere to each other.

As mentioned above in reference to FIG. 5C, the gritty top layer on the proximal end of the wedge enables the practitioner to safely position the dental wedge between teeth. The preferred embodiments also enable the practitioner to safely remove the wedge upon completion of a dental procedure in the same manner that is shown being initially positioned in FIG. 5B. FIGS. 5A–5D are a series of drawings that respectively depict wedge 30 from FIGS. 4A–4B being selected in FIG. 5A, being initially inserted into an embrasure in FIG. 5B, being positioned into the embrasure with sufficient tightness to engage the matrix band in FIG. 5C and then being removed in FIG. 5D. Note that although FIGS. 5A–5D depict a sequence, different wedges and matrix bands are shown being utilized in order to show various combinations that are possible.

As shown in FIGS. 4A–4C and 5A–5D, dental wedge 30 is comprised of (i) a body 40 having a distal insertion end 42 and a proximal end 44; and (ii) a head 60 coupled to body 40, head 60 having a distal end 62 and a proximal end 64. Also as shown, a neck 50 preferably couples head 60 to body 40. As shown, distal end 52 of neck 50 is coupled to proximal end 44 of body 40. The proximal end 54 of neck 50 is coupled to distal end 62 of head 60. Note that the proximal end 64 of head 60 is the proximal end of the wedge and that the distal insertion end 42 of the body is also the distal insertion end of the wedge.

The same numerals are used to identify the corresponding elements of each embodiment with prime symbols being used to indicate the element in reference to a different embodiment or lower case letters for embodiments that are only slightly different. So it should be understood that reference to an element and its corresponding number as shown in the drawings is also descriptive of the same element in other embodiments unless indicated otherwise by particular reference to the element. Reference is made primarily to the configuration of wedge 30 and its elements are discussed and contrasted with the corresponding elements of the other embodiments.

Figure 4A:
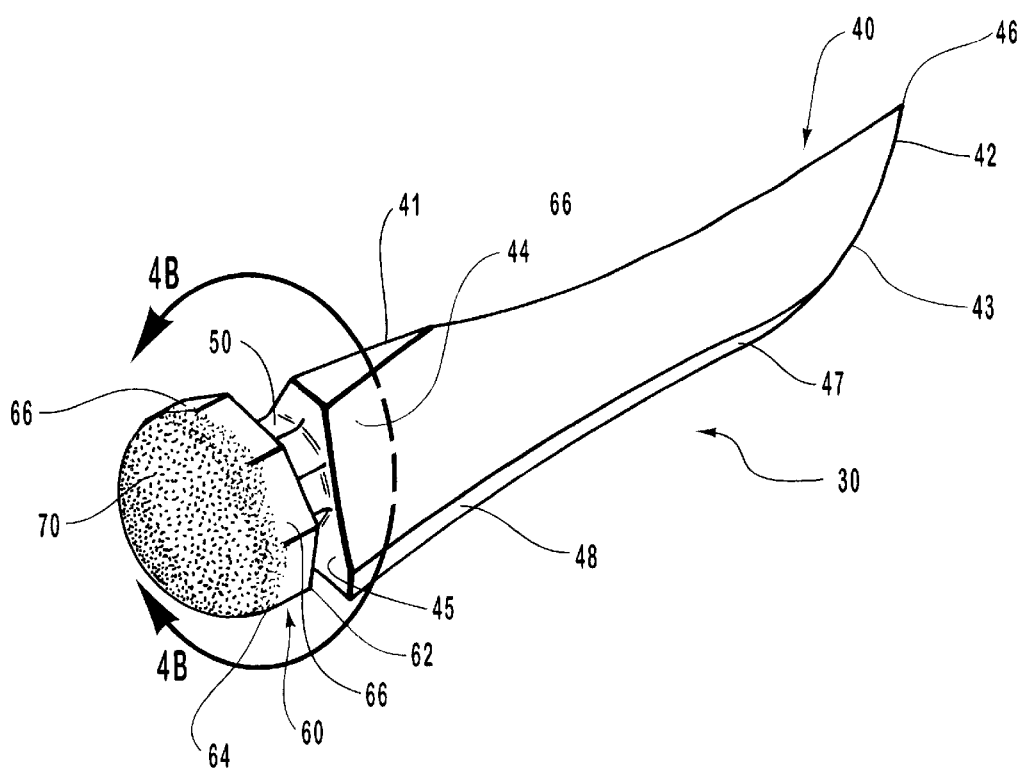
FIG. 4A is a perspective view of a dental wedge of the present invention.

The body of the wedge may have any configuration suitable for insertion into an embrasure or within an interproximal space between two teeth. As shown in FIG. 4A, the preferred configuration of the body of the wedge generally has a relatively thin distal insertion end with a bottom portion 43 that is relatively curved and which terminates at a pointed tip 46. The body preferably flares from the distal insertion end toward the proximal end 44 such that the body has a triangular cross-section of increasing size. The thin distal portion permits the practitioner to initially dispose wedge 30 between the patients' teeth. The taper of body 40 enables a practitioner to move teeth relative to each other as pressure is exerted on the wedge. More specifically, as the wedge is pushed inward, the cross section of the wedge between the teeth becomes increasingly wider, thereby enabling relative teeth movement.

Figure 5A:
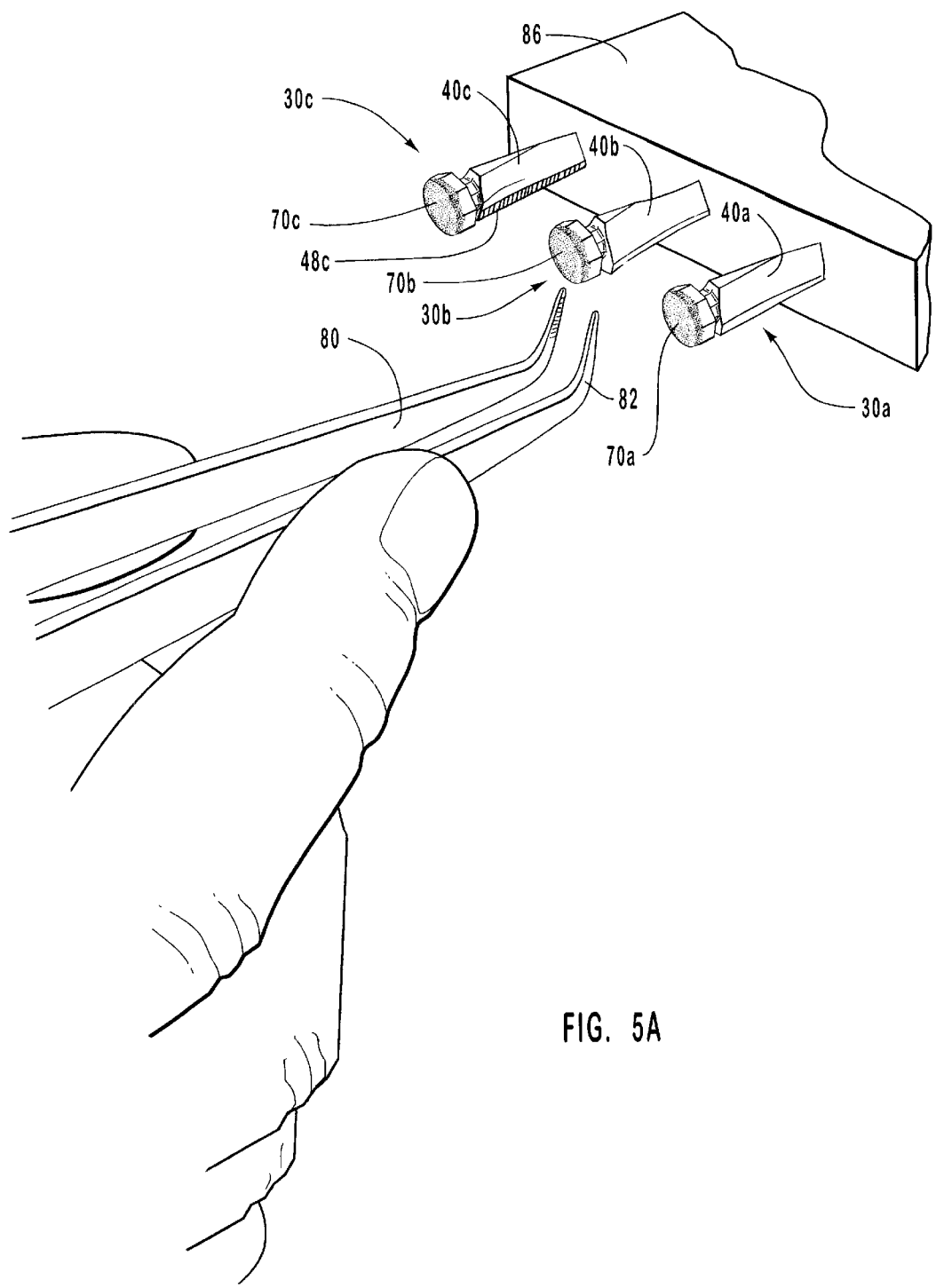
FIG. 5A is a perspective view of a user selecting a dental wedge from a set of dental wedges with different flares.

As shown in FIG. 5A, a kit may be provided of two or more wedges and the wedges may have differing configurations. More particularly, the bodies of the wedge may have different flares or tapers as depicted in FIG. 5A at 40b and 40a. The bodies of the wedges shown in FIG. 5A all have triangular cross sections, however, body 40a has a narrower base and apical angle than do the other wedge bodies 40b and 40c. In addition to the width of the base, the pitch or apical angle, the bodies of the wedges may also have differing heights. The various embodiments of wedge bodies disclosed herein, including the prior art body configurations discussed hereinabove, are examples of tapered body means for insertion within an interproximal space between two teeth. Additionally, any conventional body configuration may also be utilized.

Note that wedges 30a–c are shown in FIG. 5A standing upright in a support material 86 which is preferable for maintaining the wedges in a sterile or nearly sterile condition. As shown in FIG. 5A, a user can easily grasp a wedge with the prongs 82 or grasping end of conventional cotton pliers 80.

Figure 5B:
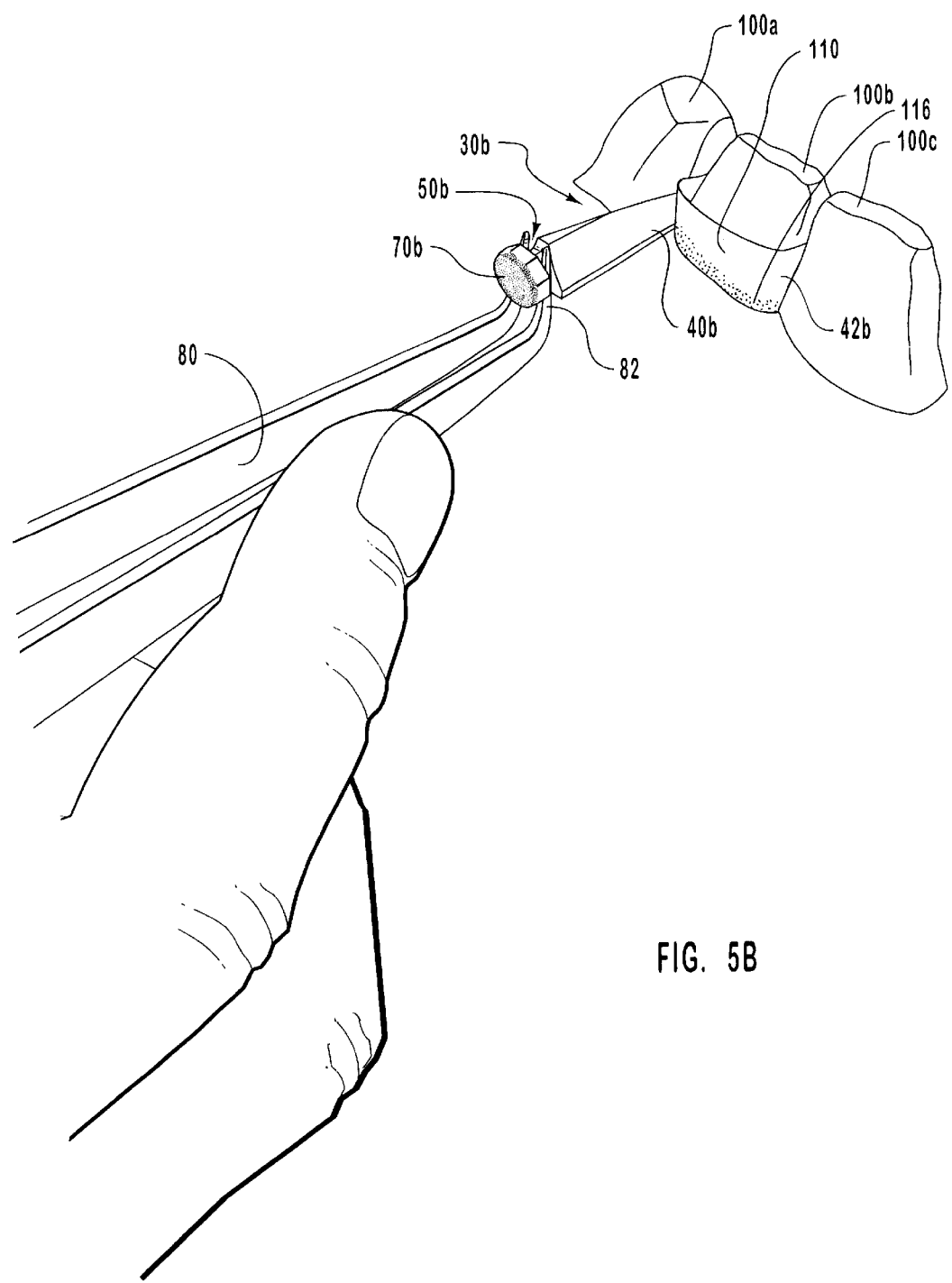
FIG. 5B is a perspective view of a user's hand grasping a dental wedge by the neck of the dental wedge with cotton tweezers and initially inserting the distal insertion end of the dental wedge into an embrasure or interproximal space adjacent a matrix band disposed about a tooth.
Figure 5C:
FIG. 5C is a perspective view of a user's hand pushing on the gritty top layer of a dental wedge with the blunt end of cotton tweezers to further insert the dental wedge between the teeth such that it is positioned as desired in the embrasure.
Figure 5D:
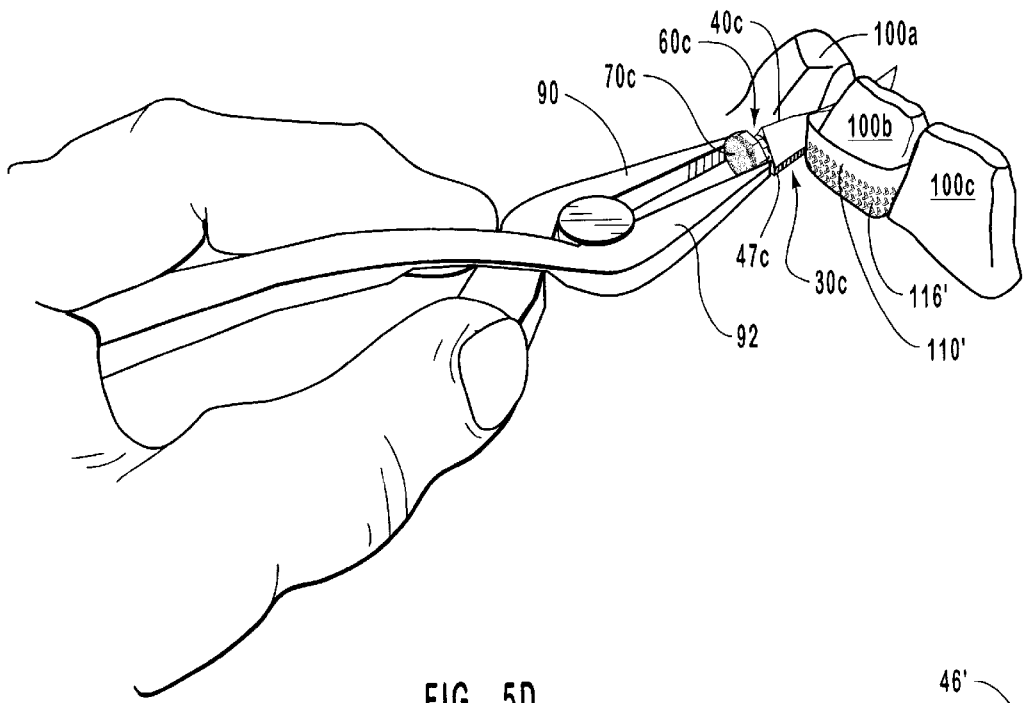
FIG. 5D is a perspective view of a user's hand pulling on the head of a dental wedge with pliers to remove the dental wedge from between the teeth.

FIGS. 5B–5D show the combined use of dental wedge 40 and matrix band 110 or matrix band 110' having a frictional engagement surface 116. As discussed above, dental wedges help to ensure that the matrix band is held against the prepared tooth. The matrix band is typically used in conjunction with a matrix band holder. Matrix bands 110, 110' and 110" are, however, shown in FIGS. 5B–5D without a dental matrix band holder primarily to enhance the viewability of the wedges. When a matrix band holder is not used, the matrix bands are held through the use various conventional methods including spot welding, soldering or the use of an elastic band, such that the band forms a sleeve or a form about the tooth. Note that solder, elastic bands and spot welding are further examples, in addition to matrix band holders, of means for positioning a matrix band around a tooth to enable the matrix band to be used in filling a dental preparation. While matrix bands 110, 110' and 110" are shown without a matrix band holder, such matrix bands are preferably held in place with a matrix band holder, especially those as disclosed in U.S. patent application Ser. Nos. 09/505,930 and 09/356,629 referenced above.

FIG. 5B shows prongs 82 grasping wedge 30b by neck 50b as distal insertion end 42b is being pushed into an interproximal space. The base or widened end of the wedge is located toward the gum line and the thin apex extends between the teeth 100b and 100c and away from the gums. The body can be initially inserted or pushed completely into position by grasping the neck and/or by pushing against the face of the proximal end of the body, such as face 45 shown in FIGS. 4A–4B. More specifically, prongs 82 are pushed against proximal end 44 of body 40 or are used to firmly grasp neck 50 while pushing against proximal end 44 to initially push wedge 30 into a desired location. The body of the wedge is then fully inserted into position as shown in FIG. 5C by urging the blunt end 84 of tweezers 80 against head 60. More particularly, blunt end 84 or any suitable instrument pushes against gritty top layer 70 on proximal end 64 of head 60 to urge body 40a of wedge 30a further between the teeth. A wedge can be easily removed from an embrasure by in the same manner shown in FIG. 5B for initial placement with prongs 82 of tweezers 80. Accordingly, wedge 30 may be pulled from the embrasure by pulling against the face of distal end 62 of head 60, such as face 63 shown in FIG. 4B with prongs 82, by firmly grasping neck 50 and pulling, or by grasping neck 50 while pulling against distal end 62. Additionally, wedge 30 may be pulled from the embrasure by grasping and pulling the head with conventional pliers as shown in FIG. 5D or by grasping and pulling the head with tweezers. While instruments such as conventional tweezers or pliers are useful for inserting and removing the dental wedges, inventive instruments which are particularly adapted for use with dental wedges such as wedges 30a–c are also disclosed in U.S. Pat. No. 6,142,781 referenced above.

Figure 4B:
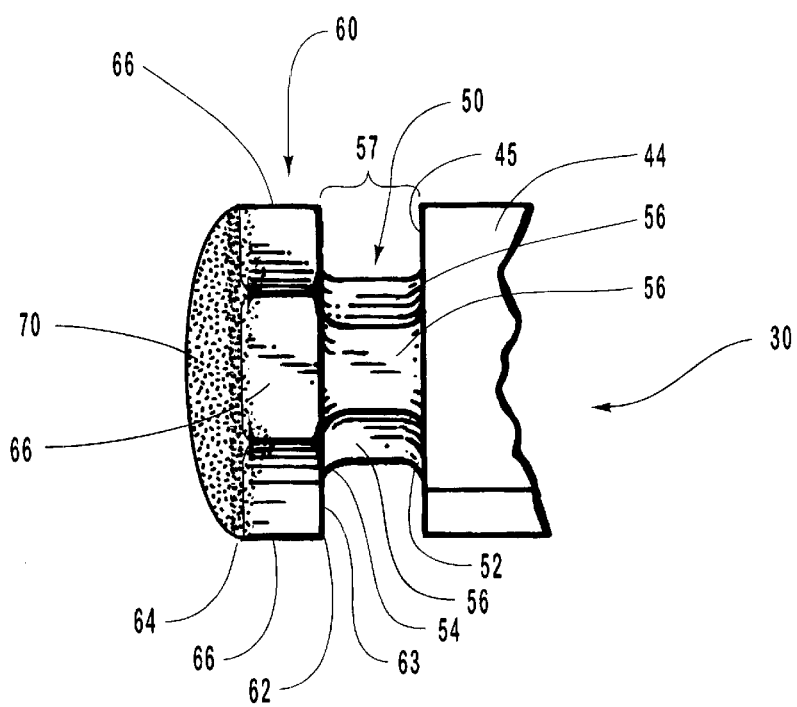
FIG. 4B is an enlarged side view of the head and neck of the wedge shown in FIG. 4A.
Figure 6:
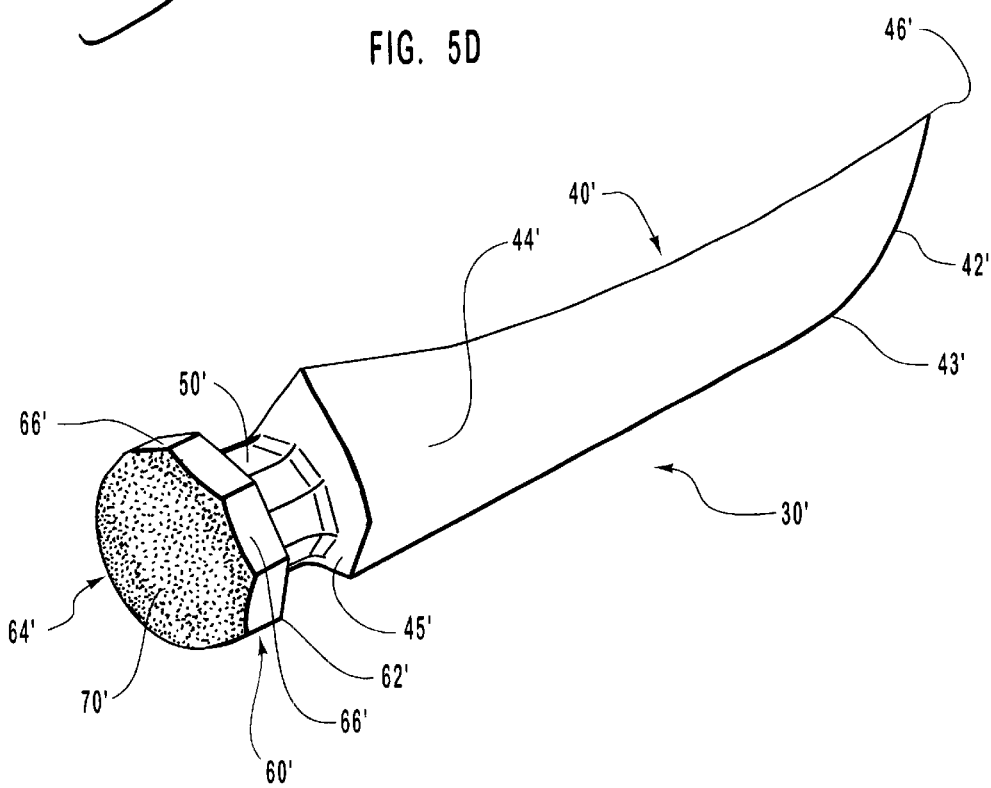
FIG. 6 is a perspective view of another embodiment of a dental wedge of the present invention which has a gritty top layer on only the proximal end of the head without extending on the faces of the head.

As shown in FIGS. 4A–4B, body 40 is preferably not entirely triangular in cross-sectional shape as the opposing corners of the base of the triangle have been truncated to provide spacing sides 47 which provide increased leverage in separating or displacing teeth. Note that the apex has been partially truncated at proximal end 44 to yield truncated apex 41. Other embodiments such as the wedge bodies 40a and 40' shown respectively in FIG. 5A and FIG. 6 are not truncated so that the sides all terminate at corners.

As previously discussed, disposing a wedge between the patient's teeth against a matrix band helps to ensure that the matrix band is held against the prepared tooth. As shown in FIGS. 5B and 5D, the matrix band may have a frictional engagement surface 116, 116' or 116". Such a frictional engagement surface is sufficiently textured or rough that dental wedges are much less likely to slip out of an embrasure once positioned against the frictional engagement surface. The increased resistance provided by the frictional engagement surfaces ensures that a matrix band will be securely held in place by a dental wedge. Accordingly, a practitioner can securely proceed with a restoration. Such frictional engagement surfaces are preferably formed by sandblasting the matrix band. However, the frictional engagement surface can be formed by any suitable process. For example, the frictional engagement surface may be formed by microetching the exterior side or a portion of the exterior side of the matrix band. A frictional engagement surface may also be formed by adhering abrasive material to the exterior side of the matrix band or a portion thereof, preferably through electrostatic methods. The frictional engagement surface may also be a sticky portion of the exterior side. Such a sticky portion may be formed, for example, by application of a suitable adhesive to the exterior side of the matrix band. Some frictional engagement surfaces may also be formed by molding such that the frictional engagement surface is formed during the molding process. Note that the frictional engagement surface may have a patterned configuration such as a series of ridges as shown in FIG. 5C at 116' or a series of arrows oriented in one direction on one side of the matrix band as shown at 116" in FIG. 5D and another series of arrows oriented in the opposite direction on the other side of the matrix band (not shown in FIG. 5D). Additional details regarding such frictional engagement surfaces are disclosed in U.S. patent application Ser. No. 09/505,930 referenced above.

The ability of the wedge to frictionally engage the matrix band is enhanced when the pushing sides of the wedge are configured with a frictional resistance surface. For example, wedge 30c shown in FIGS. 5A and 5D has pushing sides 47c with ridges 48 so that pushing sides 47 have a serrated appearance. The ridges can be separated by any suitable length and can have any suitable height. The ridges are preferably formed when the wedge is molded. Another example of a frictional resistance surface is roughened surface 48" discussed below in relation to FIG. 7. Note, however, that the pushing sides need not necessarily be configured with a frictional resistance surface as shown by wedge 30 in FIGS. 4A–4B and the identical wedge in the set shown in FIG. 5A, wedge 40b.

The frictional resistance surface of the body of the dental wedge may be formed by any suitable methods. Further, the frictional resistance surface of the body of the dental wedge may be formed by any method used to form the frictional engagement surface of the dental matrix bands. The frictional resistance surface of the dental wedge may also extend beyond the pushing sides such that the frictional resistance surface covers the entire body of the wedge or portions of the body. Any dental wedge may be configured with such a frictional resistance surface and be within the scope of the present invention. The frictional resistance surfaces on the body of dental wedges disclosed herein are examples of means for preventing a dental wedge from coming out of an embrasure after being pushed into an embrasure against a dental wedge. Note that while gritty top layer 70 is the preferred frictional resistance surface on the proximal end of the wedge, the wedges disclosed herein may have a proximal end with any of the frictional resistance surface configurations disclosed herein for the body of the wedge or for the matrix band. The gritty top layer and such other frictional resistance surfaces on the proximal end of the wedge are all examples of means for frictionally engaging an instrument used to position a dental wedge into an embrasure by pushing the proximal end of the dental wedge.

As best seen in FIG. 4B, neck 50 has a smaller diameter than distal end 62 of head 60 and proximal end 44 of body 40, thereby forming a groove 57 for placement of a dental instrument therein. Groove 57 is defined by (i) proximal end 44 of body 40; (ii) the exterior surface of neck 50; and (iii) distal end 62 of head 60. Essentially, the reduced diameter neck 50 is any depression or groove located between the head and the proximal end of the face.

FIG. 4B depicts neck 50 having eight different flat gripping surfaces 56 extending about the circumference of the surface of the neck, such that a transverse cross section of neck 50 has the shape of an octagon. Of course, the neck may have any suitable configuration. For example, the neck may have a cross-section which is generally circular, elliptical, triangular, or the neck may have four or more different flat gripping surfaces extending about the circumference of the surface of the neck such that the cross-section is that of a square, a pentagon, a hexagon, and so on. As a result of the multiple surfaces on neck 50, neck 50 may be grasped from a variety of different gripping angles and positions. Additionally, the circumference of neck 50 is preferably symmetrical.

Each neck disclosed herein is an example of neck means for receiving a grasping end of a dental instrument to move the tapered body means with respect to an interproximal space between two teeth, and for coupling the distal end of the head means to the proximal end of the tapered body means. In alternative embodiments, the surface of the neck may be textured or coated with a tacky material. Additionally, a flexible and compressible washer may be positioned around the neck. Such texturing, coatings and washers are examples frictional resistance surface of the neck and are also examples of means for preventing slipping of a dental instrument urged against the wedge, or more specifically a dental instrument used to grasp the wedge or neck.

Like neck 50, head 60 is also shown in FIGS. 4A–4B with eight different flat sides at 66. The head may have any suitable configuration, however, the head preferably is in the shape of a polygon with more than four different flat sides extending about the circumference of the head. Examples of such shapes include a pentagon, hexagon, octagon, a decagon and so on. Thus, the cross section of head 60 transverse to axis 58 may be in the shape of a pentagon, hexagon, octagon, decagon and so on. As shown, the circumference of head 60 is preferably symmetrical since each flat side has the same dimensions. While not required, the number of different flat gripping surfaces 66 of head 60 is preferably even. Similarly, the number of different flat gripping surface 56 of neck 50 is also preferably even. The flat surfaces 66 extending about the circumference of head 60 and the flat surfaces 56 extending about the circumference of neck 50 may be aligned with each other in a parallel configuration or be offset from each other such that flat surfaces 66 are not parallel with flat surfaces 56. Because of the various surfaces of the wedge, the practitioner has the option of grasping and pulling, grasping and pushing, or pushing against a variety of different structures on the wedge 30. Additionally, the head and neck may be grasped from a variety of different positions around the circumference thereof.

FIG. 6 depicts an additional embodiment of a dental wedge 30' with a body 40' without a truncated apex at its proximal end such as truncated apex 41 of body 40 of wedge 30. Note that unlike the configuration of wedge 30, the gritty top layer 70 on the proximal end of wedge 30' does not extend onto the upper portions of the faces 66' of head 60'.

Figure 7:
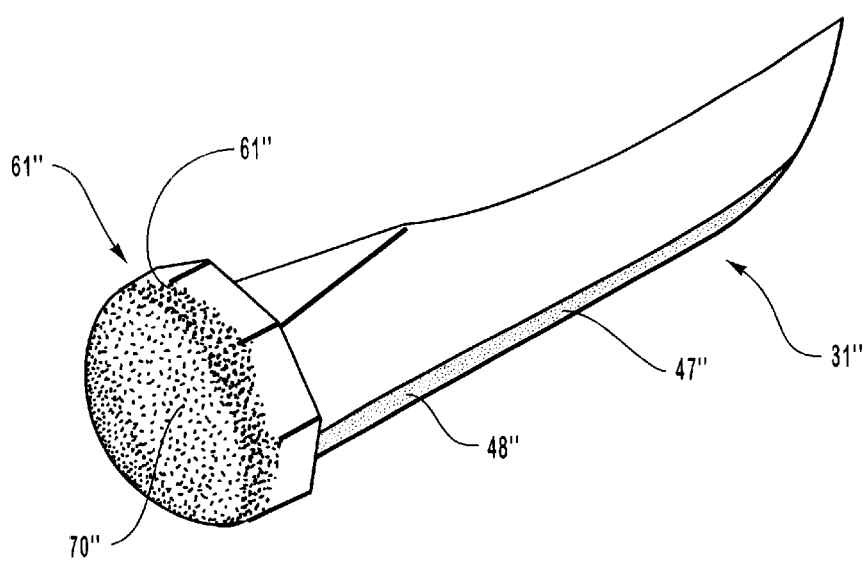
FIG. 7 is a perspective view of another embodiment of a dental wedge of the present invention which has no neck and a body which is integral with the head

FIG. 7 depicts another embodiment of a dental wedge of the present invention at 30". Head 60" of wedge 30" is directly coupled to body 40" without a neck. In such embodiments, head 60" is preferably larger than body 40" as depicted in FIG. 7. Similarly, the heads of the wedges in the other embodiments may also be larger than their respective bodies. The ability of wedge 30" to frictionally engage the matrix band is enhanced by roughened surface 48" on pushing sides 47" of wedge 30".

Figure 8:
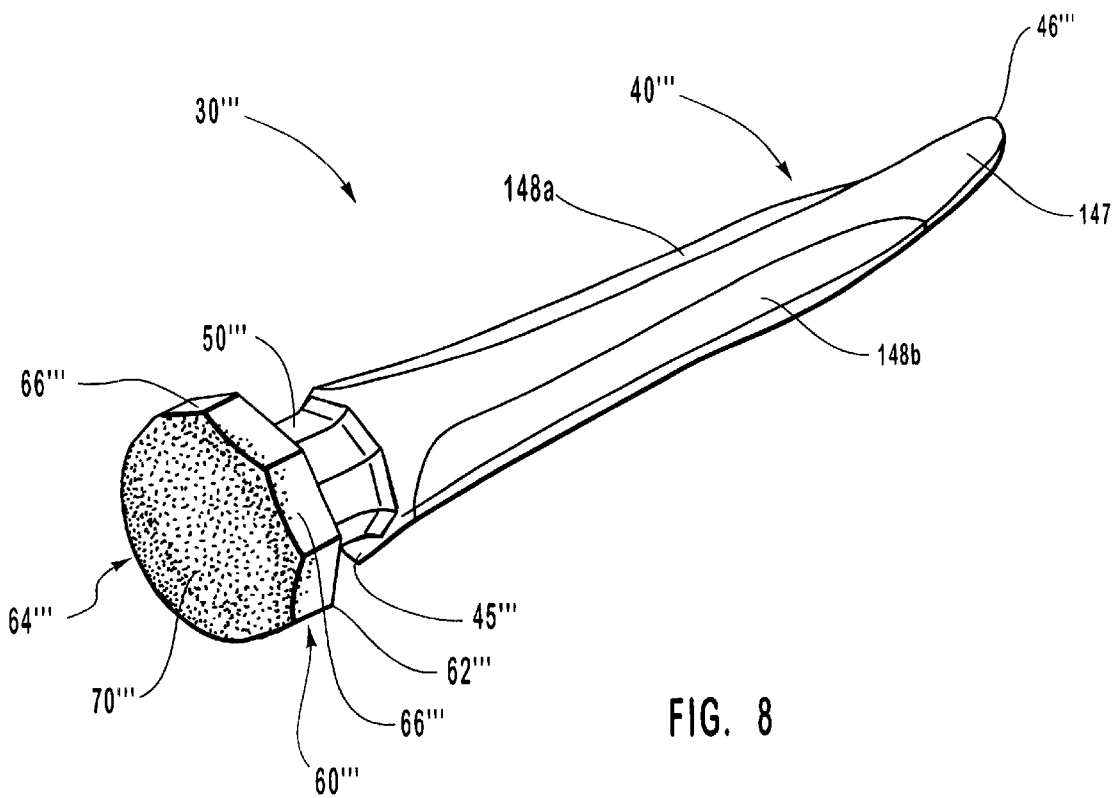
FIG. 8 is a perspective view of another embodiment of a dental wedge of the present invention which has a core and compressible side elements.

FIG. 8 depicts yet another embodiment of a dental wedge at 30'''. Wedge 30''' has a body 40''' with a core 147 and compressible side elements 148 attached to the rigid core. The compressible side elements 148a and 148b may be formed from compressible materials such as those discussed above, however the side elements are preferably formed from silicone. The side elements may be adhered onto the core or molded onto the core by the methods discussed above in relation to the positioning of the gritty top layer onto the proximal end of the wedge. The advantage of such side elements is that a tight fit is achieved when the wedge is inserted into an embrasure. Of course, an embodiment of a wedge having a body with a core and compressible side elements is not limited to configurations such as those disclosed herein or to the combined use with a gritty top layer. Core 147 may be translucent.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Patent is:

1. A dental wedge comprising:
   a tapered body means for insertion within an interproximal space between two teeth, the tapered body means having a distal insertion end,
   wherein the wedge has a proximal end opposite from the distal insertion end of the body means with a gritty top layer positioned thereon.

2. A wedge as recited in claim 1, wherein the gritty top layer is sufficiently hard that it does not noticeably compress when an instrument is pushed against the gritty top layer as the tapered body means is inserted within an interproximal space between two teeth.

3. A wedge as recited in claim 1, wherein the gritty top layer is sufficiently compressible that it noticeably compress when an instrument is pushed against the gritty top layer as the tapered body means is inserted within an interproximal space between two teeth.

4. A wedge as recited in claim 1, wherein the gritty top layer includes a grit material mixed in an attachment material.

5. A wedge as recited in claim 1, wherein the gritty top layer includes a grit material having an average particle size ranging from about 50 microns to about 80 mesh.

6. A wedge as recited in claim 1, wherein the gritty top layer is positioned on the proximal end of the wedge as a coating.

7. A wedge as recited in claim 1, wherein the gritty top layer is positioned on the proximal end of the wedge by a molding process.

8. A wedge as recited in claim 1, wherein the proximal end of the wedge is a proximal end of a head.

9. A wedge as recited in claim 1, wherein the proximal end of the wedge is a proximal end of a head and wherein the head is coupled to the body means by a neck.

10. A wedge as recited in claim 1, wherein the tapered body means is formed from plastic.

11. A dental wedge comprising:
    a tapered body configured to be inserted within an interproximal space between two teeth, the tapered body having a distal insertion end,
    wherein the wedge has a proximal end opposite from the distal insertion end of the tapered body with a gritty top layer positioned thereon.

12. A wedge as recited in claim 11, wherein the gritty top layer is sufficiently hard that it does not noticeably compress when an instrument is pushed against the gritty top layer as the tapered body is inserted within an interproximal space between two teeth.

13. A wedge as recited in claim 11, wherein the gritty top layer is sufficiently compressible that it noticeably compresses when an instrument is pushed against the gritty top layer as the tapered body is inserted within an interproximal space between two teeth.

14. A wedge as recited in claim 11, wherein the gritty top layer includes a grit material mixed in an attachment material.

15. A wedge as recited in claim 11, wherein the gritty top layer includes a grit material having an average particle size ranging from about 50 microns to about 80 mesh.

16. A wedge as recited in claim 11, wherein the gritty top layer is positioned on the proximal end of the wedge as a coating.

17. A wedge as recited in claim 11, wherein the gritty top layer is positioned on the proximal end of the wedge by a molding process.

18. A wedge as recited in claim 11, wherein the proximal end of the wedge is a proximal end of a head.

19. A wedge as recited in claim 11, wherein the proximal end of the wedge is a proximal end of a head and wherein the head is coupled to the body by a neck.

20. A dental wedge comprising:
    a tapered body configured to be inserted within an interproximal space between two teeth, the tapered body having a distal insertion end,
    a head coupled to the tapered body by a neck, wherein the head has a proximal end opposite from the distal insertion end of the body,
    a gritty top layer positioned on the proximal end of the head.

* * * * *

UNITED STATES PATENT AND TRADEMARK OFFICE
CERTIFICATE OF CORRECTION

PATENT NO. : 6,375,463 B1
DATED : April 23, 2002
INVENTOR(S) : Bruce McLean and Dan E. Fischer It is certified that error appears in the above-identified patent and that said Letters Patent is hereby corrected as shown below:

Column 1,
Line 26, after "particularly, the" change "inventions" to -- invention --

Column 2,
Line 13, after "distorted" please insert -- . --
Line 62, after "a composite material" please insert -- . --

Column 3,
Line 1, after "To enhance" change "an" to -- a --

Column 4,
Line 53, after "integral with the head" please insert -- . --

Column 11,
Line 31, after "that it noticeably" change "compress" to -- compresses --

Signed and Sealed this

Eighth Day of October, 2002

Attest:

JAMES E. ROGAN
Attesting Officer
Director of the United States Patent and Trademark Office